US012557984B2

(12) United States Patent
Tavakkoli et al.

(10) Patent No.: US 12,557,984 B2
(45) Date of Patent: Feb. 24, 2026

(54) METHOD AND APPARATUS FOR MEASURING RELATIVE AFFERENT PUPILLARY DEFECTS

(71) Applicant: NEVADA RESEARCH & INNOVATION CORPORATION, Reno, NV (US)

(72) Inventors: Alireza Tavakkoli, Reno, NV (US); Stewart Zuckerbrod, Bellaire, TX (US)

(73) Assignee: Nevada Research & Innovation Corporation, Reno, NV (US)

( * ) Notice: Subject to any disclaimer, the term of this patent is extended or adjusted under 35 U.S.C. 154(b) by 351 days.

(21) Appl. No.: 18/253,447

(22) PCT Filed: Nov. 16, 2021

(86) PCT No.: PCT/US2021/072431
§ 371 (c)(1),
(2) Date: May 18, 2023

(87) PCT Pub. No.: WO2022/109546
PCT Pub. Date: May 27, 2022

(65) Prior Publication Data
US 2023/0404388 A1      Dec. 21, 2023

Related U.S. Application Data

(60) Provisional application No. 63/116,207, filed on Nov. 20, 2020.

(51) Int. Cl.
*A61B 3/06* (2006.01)
*A61B 3/032* (2006.01)
(Continued)

(52) U.S. Cl.
CPC .............. *A61B 3/063* (2013.01); *A61B 3/032* (2013.01); *A61B 3/111* (2013.01); *A61B 3/145* (2013.01)

(58) Field of Classification Search
CPC ......... A61B 3/032; A61B 3/063; A61B 3/111; A61B 3/14; A61B 3/145; A61B 3/11
See application file for complete search history.

(56) References Cited

U.S. PATENT DOCUMENTS

| | | | |
|---|---|---|---|
| 11,229,358 B2 * | 1/2022 | Karargyris | .......... A61B 3/0091 |
| 2009/0213329 A1 | 8/2009 | Kandel et al. | |

(Continued)

OTHER PUBLICATIONS

International Search Report and Written Opinion dated Feb. 7, 2022 which was issued in connection with PCT/US2021/072431 which was filed on Nov. 16, 2021, 7 pages.

*Primary Examiner* — Nelson M Rosario

(57) ABSTRACT

Methods and systems for administering a modular and/or flexible eye test to patients are presented that leverages on the visualization, processing, and eye tracking capabilities of a head mounted display (HMD). In an embodiment, a method for evaluating the pupillary responses includes using a head mounted display (HMD) worn by a patient to expose a first eye to light stimulation in accordance with a relative afferent pupillary defects (RAPD) eye test, an imaging device of the HMD receiving image data of the first eye, then exposing a second eye to the same RAPD eye test and receiving image data of the second eye, and generating at least one test result by using the image data of the first eye and the image data of the second eye.

17 Claims, 6 Drawing Sheets

(51) Int. Cl.
    *A61B 3/11*          (2006.01)
    *A61B 3/14*          (2006.01)

(56)             References Cited

U.S. PATENT DOCUMENTS

| | | | |
|---|---|---|---|
| 2016/0270656 A1 | 9/2016 | Samec et al. | |
| 2017/0347878 A1 | 12/2017 | Milea et al. | |
| 2017/0365101 A1 | 12/2017 | Samec et al. | |
| 2018/0333092 A1* | 11/2018 | Roshan | ................ A61B 3/0091 |

* cited by examiner

METHOD AND APPARATUS FOR MEASURING RELATIVE AFFERENT PUPILLARY DEFECTS

CROSS REFERENCE TO RELATED APPLICATION

This application claims the benefit of U.S. Provisional Patent Application No. 63/116,207 filed on Nov. 20, 2020, the contents of which provisional application are hereby incorporated by reference for all purposes.

FIELD OF THE INVENTION

The invention generally relates to providing a modular and/or flexible eye test for administering to patients that leverages the visualization, processing, and eye tracking capabilities of a head mounted display (HMD) such as a virtual reality headset. More specifically, disclosed are methods and apparatus for quickly and accurately testing the relative afferent pupillary defects (RAPD) of a patient and using the RAPD test data to assess and/or diagnose the level of neurological deficits and/or disorders.

BACKGROUND

The field of Ophthalmology is a branch of medicine and surgery which deals with the diagnosis and treatment of human eye and brain disorders. A partial list of some common eye and brain diseases diagnosed by Ophthalmologists includes Glaucoma, Ischemic Optic Neuropathy (ION), traumatic brain injury (TBI), Multiple Sclerosis (MS), strokes, brain tumors and aneurysms. In order to diagnose patients who may have one or more of such diseases, patients may undergo eye examinations that measure responses of their eyes to visual stimuli. One such assessment considers the relative difference in the amount and/or rate of pupillary constriction and/or dilation in response to a light stimulus. Ophthalmologists thus measure or test a patient's sensitivity to light in order to identify disorders of the eye, the optic nerve, the optic chiasm, the visual pathways to the brain, and the brain itself.

A relative afferent pupillary defect (RAPD) is a critically important ophthalmological examination result that indicates a defect (lesion) in the pupil pathway on the afferent side. The RAPD is relative to the fellow eye and occurs because of the bilateral and equal innervation of the pupils in normal individuals, and the RAPD manifests as a difference in pupillary light reaction between the two eyes. Thus, the RAPD is an assessment known for measuring a patient's pupillary reactions and is used by ophthalmologists and optometrists for testing purposes. This test, also known as the "swinging flashlight" test, can be administered by shining a flashlight into one eye and then waiting and watching for the pupils of both eyes to contract or constrict. The muscles responsible for constricting the pupils respond reflexively in both eyes to the light stimulus. Thus, in a healthy person, when the pupil under the flashlight constricts, the other pupil will constrict at the same rate and by the same amount. The clinician then rapidly swings or moves the flashlight to the other eye (the second pupil) and observes the pupils again. The observed constriction or dilation of the second pupil could be indicative of neurological damage to one of the visual pathways; photoreceptors, optic nerve, optic chiasm, or other parts of the brain responsible for autonomic responses (which are involuntary or unconscious responses). The pathologic response that characterizes the RAPD includes the following: 1) the light reaction causes pupil constriction in both eyes when the light shines in the normal eye, and (2) dilatation of the pupils in both eyes when the light stimulus is rapidly transferred from the normal eye to the pathologic eye. Many of the elements of the visual pathways are complex and an eye doctor therefore must pay very close attention to the timing of the flashlight movements, to the minute changes in pupillary size, and to the speed of any changes.

Head-mounted display (HMD) devices, such as Virtual Reality (VR) headsets, are known, and perhaps the best known use of such VR headsets is to visually simulate a user's physical presence in virtual spaces. Such simulations typically include a three-hundred and sixty (360) degree view of the user's surrounding virtual space so that when the user turns his head he or she can view different portions of the surrounding space.

HMD devices have also been used for visual field testing of patients. However, there currently are no eye testing HMD systems capable of efficiently and comprehensively testing a patient's relative afferent pupillary responses from the standpoint of allowing an emergency room doctor, an ophthalmologist, an optometrist and/or a patient to select obtain test results for use in diagnosing the early onset of neurological disorders. Thus, the inventors recognized that there is a need for systems and methods for providing a modular and/or a flexible eye test that leverages the stereo vision and eye tracking capabilities of an HMD to administer one or more RAPD tests.

SUMMARY OF THE INVENTION

Presented are solutions for evaluating pupillary responses of a patient to light stimuli. In a first aspect, a method of evaluating the pupillary responses of a patient includes using a head-mounted display (HMD) to alternately expose a first eye and then a second eye of the patient to light stimulation in successive intervals. In some implementations, the light stimulation is provided to the first and second eyes of a patient by at least one real or virtual light source controlled by at least one computing device. When the eyes are exposed to light stimulation, the process may include concurrently capturing image data of the first eye and then image data of the second eye with at least one imaging device controlled by the at least one computing device of the HMD.

In some embodiments, at least one computing device determines a center point of the first eye and its pupil within the image data of the first eye and a center point of the second eye and its pupil within the image data of the second eye; obtains first image data of a first half of the first eye having an edge defined by a line of pixels intersecting the determined center point of the first eye; obtains second image data of a second half of the second eye, the second half of the second eye opposing the first half of the first eye and having an edge defined by a line of pixels intersecting the determined center point of the second eye; and generates a composite image of the patient's eyes and pupils by using the first image data and the second image date. In some embodiments, the first and second image data may include pupil measurements including radius, major axis length, and minor axis lengths. In some embodiments the HMD evaluates the composite image, while in other implementations a separate computing device evaluates the composite image.

In a second aspect, a system is presented for evaluating the pupillary responses of a patient. In some embodiments, the system includes at least one real or virtual light source for alternately exposing a first eye and a second eye, respectively, to light stimulation in successive intervals; at least one image capturing device for concurrently capturing image data from the first eye and from the second eye, respectively; and an image manipulation system. The image manipulation system may include one or more processors configured to determine a center point of the first eye within the image data of the first eye and a center point of the second eye within the image data of the second eye; obtain image data of a first half of the first eye having an edge defined by a line of pixels intersecting the determined center point of the first eye; obtain image data of a second half of the second eye, the second half of the second eye opposing the first half of the first eye and having an edge defined by a line of pixels intersecting the determined center point of the second eye; create a composite image including the image data of the first half of the first eye and the image data of the second half of the second eye; and generate a composite image for evaluation.

In a third aspect, a method of evaluating the pupillary responses of a patient is provided wherein an HMD is used to alternately expose a first eye and a second eye of a patient to light stimulation in successive intervals. The light stimulation may be provided by real or virtual light sources controlled by at least one computing device, and during the exposure of eyes to the light the HMD concurrently captures, with a virtual imaging device controlled by at least one computing device of the HMD, image data of the first eye and of the second eye. The at least one computing device converts the image data of the first eye and of the second eye to binarized images of the first eye and the second eye that separate a pupil portion from a non-pupil portion; determines a center point of the first eye within the image data of the first eye and a center point of the second eye within the image data of the second eye; obtains image data of a first half of the first eye having an edge defined by a line of pixels intersecting the determined center point of the first eye; obtain image data of a second half of the second eye, the second half of the second eye opposing the first half of the first eye and having an edge defined by a line of pixels intersecting the determined center point of the second eye; creates a composite image including the image data of the first half of the first eye and the image data of the second half of the second eye; and generates a composite image for evaluation.

In a fourth aspect, a specially-designed VR device (which may be in the form of a HMD) is provided for detecting an ocular and/or neurological dysfunction of a patient. In some embodiments, the specially-designed VR device includes a first eye scope for exposing a first eye to a series of light flashes and for detecting a pupillary reflex of the first eye for each flash, wherein the first eye scope includes an ocular aperture, a light aperture, and a monitoring aperture. The specially-designed VR device also includes a second eye scope for detecting a pupillary reflex of a second eye of the patient for each light flash, the second eye scope including an ocular aperture and a monitoring aperture. In addition, the specially-designed VR device includes a first real or virtual light source for generating the series of light flashes through the light apertures, wherein each light flash in the series of light flashes varies by at least one of chromatically, location in the visual field, and luminosity from the other light flashes in the series of light flashes.

BRIEF DESCRIPTION OF THE DRAWINGS

Features and advantages of some embodiments of the present disclosure, and the manner in which the same are accomplished, will become more readily apparent upon consideration of the following detailed description taken in conjunction with the accompanying drawings, which illustrate preferred and example embodiments and which are not necessarily drawn to scale, wherein.

DETAILED DESCRIPTION

In general, and for the purposes of introducing concepts of embodiments of the present disclosure, disclosed herein are Virtual Reality (VR) methods and systems for efficiently measuring pupillary responses of a patient's eyes using a head mounted display (HMD). VR Relative Afferent Pupillary Defect (RAPD) tests are disclosed which leverage the stereo vision and eye tracking capabilities of the HMD to test and/or measure pupillary responses which make it possible to diagnose potential neurological disorders. More specifically, in some embodiments a system including a HMD and one or more computers is configured to efficiently administer a RAPD test to a patient. The eye test is flexible and may be administered by an Ophthalmologist, by an Optometrist, by a general practitioner, or by the patient.

In some embodiments, eye examinations are performed using a HMD worn by a patient that is configured to present images to each eye of the patient individually, and with regard to some tests to present images to both eyes simultaneously. In some implementations, the HMD is able to control lighting conditions, such as brightness, during an eye examination and thus may provide more accurate and reliable test results. The HMD may also be configured to change the visual environment experienced by the patient during testing. For example, the HMD may be capable of providing an experience involving a natural setting which may cause the patient to feel less stressful during testing. Moreover, the HMD (or another component of the overall system, such as a computer) may be configured to identify abnormal test results in real-time and, in some cases, modify the eye test and/or eye examination accordingly. For example, one or more tests scheduled to be performed during an eye examination of a particular patient can be modified or removed and/or new or different tests can be added.

Figure 1:
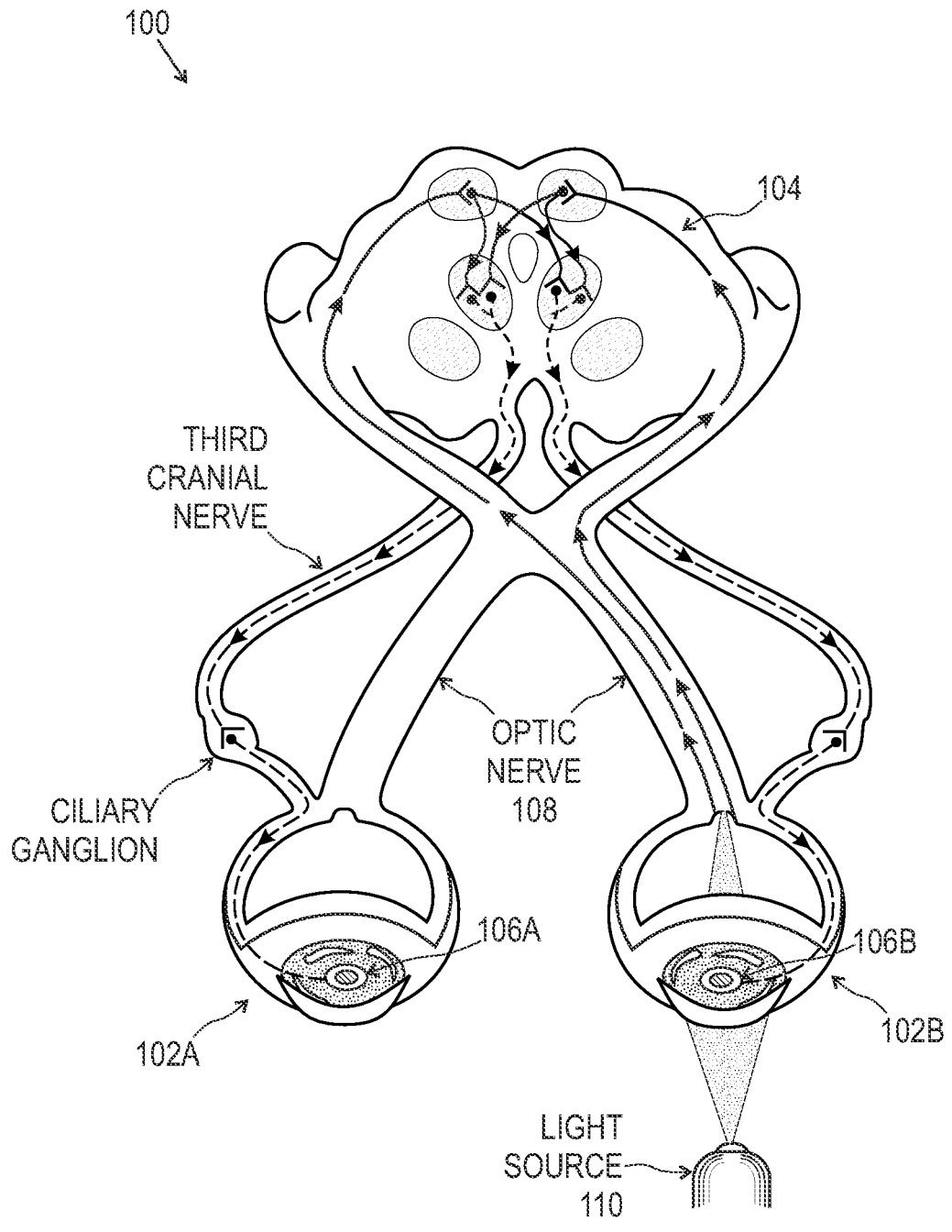
FIG. 1 is a top view illustration of the visual efferent and afferent pathways of the human eyes.

FIG. 1 is a top view 100 of the visual efferent and afferent pathways of human eyes 102A, 102B. Light sensed by the eye will invoke a signal in the brain 104 to change (dilate or constrict) the pupils 106A, 106B in order to allow the appropriate amount of light to reach the photoreceptors. Note that the optic nerve 108 splits into two paths and then reaches the brain 104. Therefore, when someone shines a light source 110 into one eye 106B of a healthy person, the pupils of both eyes 102A and 102B of that person will constrict at the same rate.

Figure 2A:
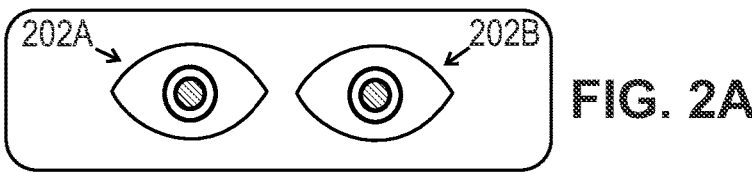
FIGS. 2A to 2D illustrate how a Relative Afferent Pupillary Defect (RAPD) test, sometimes referred to as the swinging flashlight test (SFT), is performed.
Figure 2B:
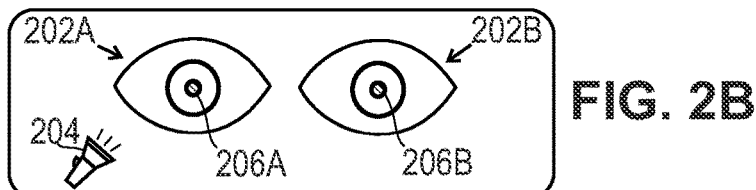
Figure 2C:
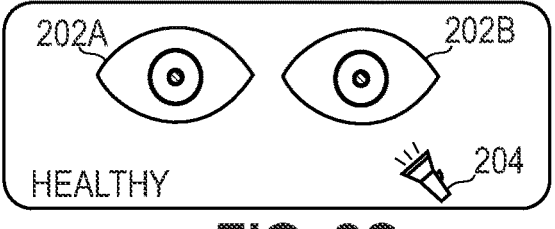
Figure 2D:
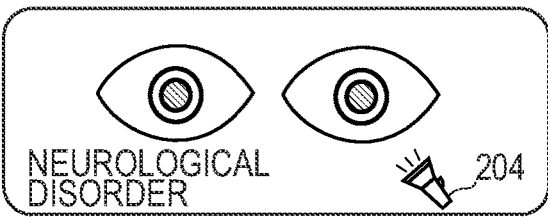

FIGS. 2A to 2D illustrate how the RAPD test, sometimes known as the swinging flashlight test (SFT), is performed. FIG. 2A illustrates both eyes 202A and 202B of a person in rest positions having normal pupil dilation. In FIG. 2B, a flashlight 204 is shined into one eye 202A, and for a normal person both pupils 206A and 206B constrict at the same rate. In FIG. 2C, the flashlight 204 is moved in a rapid manner to the other eye 202B, and in a healthy person, the pupils remain constricted. However, as shown in FIG. 2D, if when the flashlight 204 is moved in a rapid manner to the other eye 202B the pupils 206A, 206B dilate then that indicates that the person being tested suffers from a neurological disorder or a neuro-ocular disorder.

Figure 3:
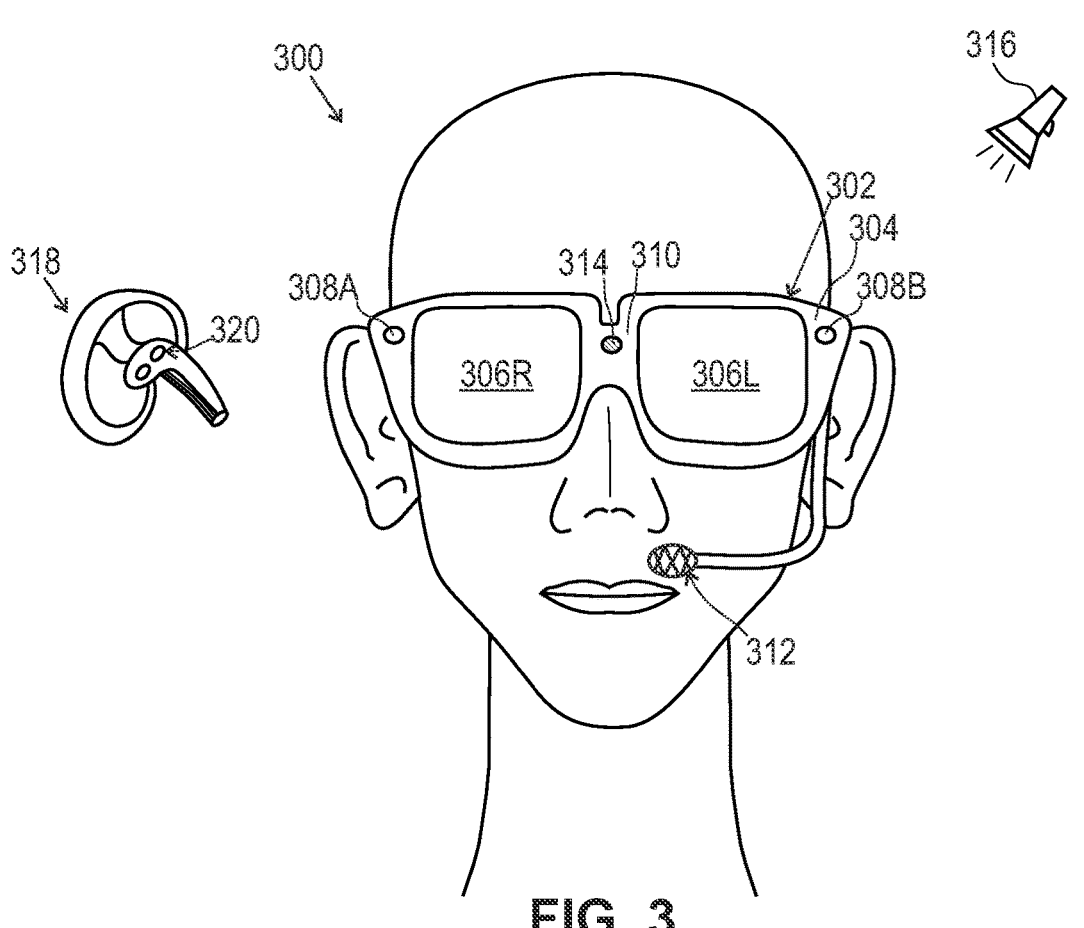
FIG. 3 illustrates a front view of a head-mounted display (HMD) that may be worn by a patient in accordance with aspects of the disclosure.

FIG. 3 is a front view of an example of a head-mounted display (HMD) 302 that may be worn by a patient 300 in accordance with aspects of the disclosure. The HMD 300 may include a frame 304 that includes a bridge 310 configured for resting on the nose of a patient. The frame 304 houses a first optical display 306L positioned in front of the left eye of the patient, and a second optical display 306R that is positioned in front of the right eye of the patient. The first optical display 306L and second optical display 306R are components of an image display system of the HMD 302, and both include interior optical display surfaces (not shown). The interior optical display surfaces reflect light towards the patient's left eye and right eye and include supporting electronic components (not shown). In some embodiments, the HMD 302 also includes one or more sensors 308A, 308B, a microphone 312 and a camera 314. Although the binocular HMD 302 shown in FIG. 3 resembles conventional eyeglasses, the HMD could also be in the form of goggles, or a helmet, or a visor and the like.

The projection and presentation systems employed by HMDs can be characterized as binocular, bi-ocular, and monocular systems. Binocular systems present a separate image to each of the user's eyes, bi-ocular systems present a single image to both of the user's eyes, and monocular HMD systems present a single image to one of the user's eyes. Each of these systems or combinations thereof could be used in accordance with various types of eye tests in accordance with the methods disclosed herein. For example, HMD 302 of FIG. 3 may utilize a binocular system and/or be configured to operate as a binocular system and thus be capable of presenting a distinct image to each of the patient's eyes during an eye test.

In general, the HMDs described herein are configured to display simulated (e.g., computer-generated) images of a virtual environment. Thus, the HMD 302 can generate and present completely immersive "virtual reality" environments to a patient during an eye examination. Convincing virtual reality images that are immersive typically require a helmet-type or goggle-type device which form-fit to a user's or patient's face and head (usually via straps) so that the HMD forms an enclosed area around the user's eyes. In addition, some HMDs include audio speakers such as over-ear headphones (not shown in FIG. 3) that can be used to provide audio prompts, background music and/or atmospheric sounds and the like, while also minimizing or preventing ambient noise from being heard by the patient. In the context of this disclosure, the term "ambient noise" means the sound that is already available in the room or space in which the patient is located before any other sound(s) is/are added, and the term "ambient light" means the light that is already available in the room or space in which the patient is located before any other lighting is added. Thus, in some embodiments an HMD in the form of goggles or in the form of a helmet also minimizes or prevents contamination from ambient light from entering the patient's eyes while the over ear headphones keep out or minimize ambient sound(s).

As shown in FIG. 3, in some implementations the HMD 302 may also include a microphone 312 to receive audio input from a patient during an eye test. It should also be understood that, in some embodiments the HMD 302 may be configured to display computer-generated (or simulated) images that are integrated into real world content perceived by the patient, which is referred to as "augmented reality" and which does not require an immersive structure.

In some embodiments disclosed herein, a specialized HMD may be used by the patient that is specifically designed for performing eye examinations. In other instances, off-the-shelf HMDs currently for sale by many manufacturers may be used to administer eye tests when configured to perform eye tests in accordance with methods disclosed herein. In particular, the various methods described below could be performed using an HMD that was designed for another purpose (for example, an HMD designed for gaming and/or other types of entertainment purposes). For example, in some implementations in accordance with the methods disclosed herein, VR headsets manufactured by Occulus, the HTC company, and/or Microsoft Corporation, may be utilized in addition to traditional equipment.

Referring again to FIG. 3, as mentioned above the binocular HMD 302 includes an optical display 306L for the patient's left eye and an optical display 306R for the patient's right eye, which are configured to permit content to be presented to each of the patient's eyes individually, as well as to both the left and right eyes collectively. The optical displays 306L and 306R may completely surround or wrap-around one or both eyes of the patient. For example, the interior portions of the frame 304 and/or the bridge 310 may be designed to ensure that light (e.g., an image) presented to one eye cannot be seen by the other eye. For example, a partition (not shown) may be formed within the bridge 310 (between the eyes) that prevents light from entering the right eye when a particular test requires testing of only the left eye, and vice-versa. Thus, the HMD 302 allows digital images to be shown to one eye, while limiting what, if anything, can be seen by the other eye depending on the requirements of a specific eye test.

The HMD 302 can also include an electronics module (not shown) for processing digital content (for example, images and/or video), and/or for gathering and/or processing data gathered or obtained from the eyes of the patient. Such an electronics module may include one or more specially-designed processors or other types of processors capable of executing processor-executable instructions to operate in the manner(s) disclosed herein. The electronics module may also be configured for optimizing the digital content to be presented to the patient, for analyzing the patient's pupillary light response data collected by the one or more sensors 308A, 308B, for analyzing patient audio responses received by the microphone 312, and the like. In some embodiments, the electronics module may provide at least some analysis (for example, test results) to be performed locally by the HMD 302. As will be discussed below, in some embodiments the HMD 302 may be operably connected to one or more other computing devices (such as Smart phones, tablet computers, laptop computers, server computers, and the like) that are also configured for performing some or all of such tasks. The electronics module and HMD 302 can be powered by a battery (not shown), or through a wired or wireless connection to a power source (not shown).

In some implementations, the sensors 308A, 308B coupled to the frame 304 may be operably connected to one or more of the optical displays 306R, 306L and may function to monitor various aspects of the patient's local environment. For example, one or both of the sensors 308A, 308B may include additional temperature and/or humidity sensors for providing data associated with the comfort level in the test area for the patient and/or a light sensor which can track ambient light levels, and the like, and the camera 314 may be operable to provide additional visual data about the patient's eyes, pupils, and other ocular images. The HMD 302 may also include one or more interior or inner-facing optical sensors or cameras (not shown) which may be configured to monitor and/or capture the patient's pupillary responses.

In some embodiments, the camera 314 may be operable to record the radiance of an external light source 316 and then to present a video recording of the light source 316 alternatively to each eye, for example, during performance of an eye test. In an implementation, the first optical display 306R shows the recording of the external light source to the right eye of a patient while the second optical display 306L is off. After an internal camera (not shown) records the pupil light responses from both the right and left eyes of the patient, then the second optical display 306L will turn on and show the recording of the light source to the left eye of the patient while the first optical display 306R is turned off. Once again, the pupil light responses of both the right and left eyes of the patient are recorded, and in implementations a RAPD will then be computed based on the pupil light responses of both eyes for the entire recording time.

Referring again to FIG. 3, one or more speakers or headphones (not shown) may also be operably connected to the frame 302 and may be used to provide instructions and/or prompts to the patient during an eye examination. It should be understood that one or more other types of sensors could also be utilized, and that the HMD may also incorporate or include a hand controller 318. The hand controller 318 may include one or more control buttons 320 and include motion sensing circuitry (not shown) operable to, for example, capture hand motion input from the patient during an eye test. The hand controller 318 may also provide motion data which may be analyzed during testing and/or stored for analysis. In addition, some embodiments may include one or more additional cameras (not shown) for providing data concerning the physical test room or area surrounding the patient, which cameras may or may not be connected to the frame 302.

Figure 4:
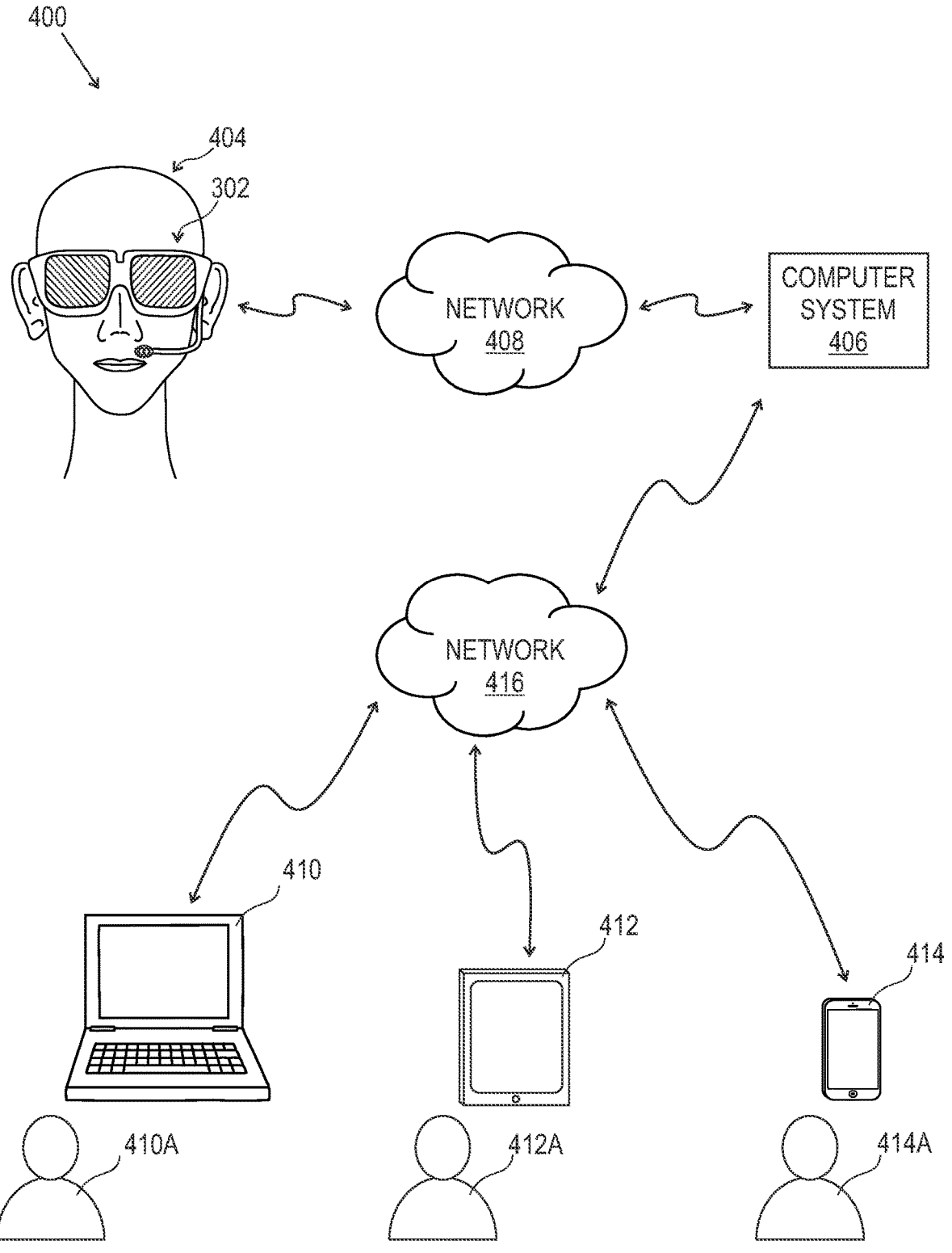
FIG. 4 is a block diagram illustrating components of an eye examination system for performing eye tests in accordance with some embodiments of the disclosure.

FIG. 4 is a block diagram illustrating components of an eye examination system 400 for performing eye tests in accordance with some embodiments. The HMD 302 is worn by a patient 404 and is operably connected to a computer system 406 (for example, a server computer) via a network 408, such as the Internet or a private computer network. The HMD 302 and/or the computer system 406 are configured to perform some or all of the methods described herein. In particular, in some implementations the system 400 can be distributed between the HMD 302 and the computer system 406.

Referring again to FIG. 4, in some embodiments one or more additional electronic devices 410, 412, 414 are included, and such devices may be controlled by an ophthalmologist 410A, an optometrist 412A, and/or an optical clinician 414A and the like. One or more of the electronic devices 410, 412 and 414 may be operably connected to the HMD 302 via a computer network 416 and/or to the computer system 406. Thus, one or more doctors and/or clinicians may be able to control and/or utilize the HMD 302 to conduct eye tests on the patient 404. The computer network 416 can be the same as, or distinct from, the network 408. Thus, in some implementations one or more of the additional electronic devices 410, 412 and 414 may be operably connected to the HMD 302 via the Internet or via local wireless networks such as WiFi networks or Bluetooth networks. In addition, one or more of the electronic devices 410, 412 and 414 may comprise a server computer, a client computer, a personal computer (PC), a user device, a tablet computer, a laptop computer, a personal digital assistant (PDA), a cellular telephone or Smartphone, a web appliance, a wearable electronic device, a gaming device, a music player, or any electronic device capable of executing a set of instructions (sequential or otherwise) that specify actions to be taken by the electronic device in accordance with methods disclosed herein.

The eye examination system 400 permits ophthalmologists, optometrists, eye clinicians and the like to supervise the patient 404 while eye tests are being conducted. While the HMD 302, computer system 406, and the electronic devices 410, 412, 414 are depicted as wirelessly communicating with one another, in some configurations one or more of the components of the eye examination system 400 can be connected together via wires.

Figure 5B:
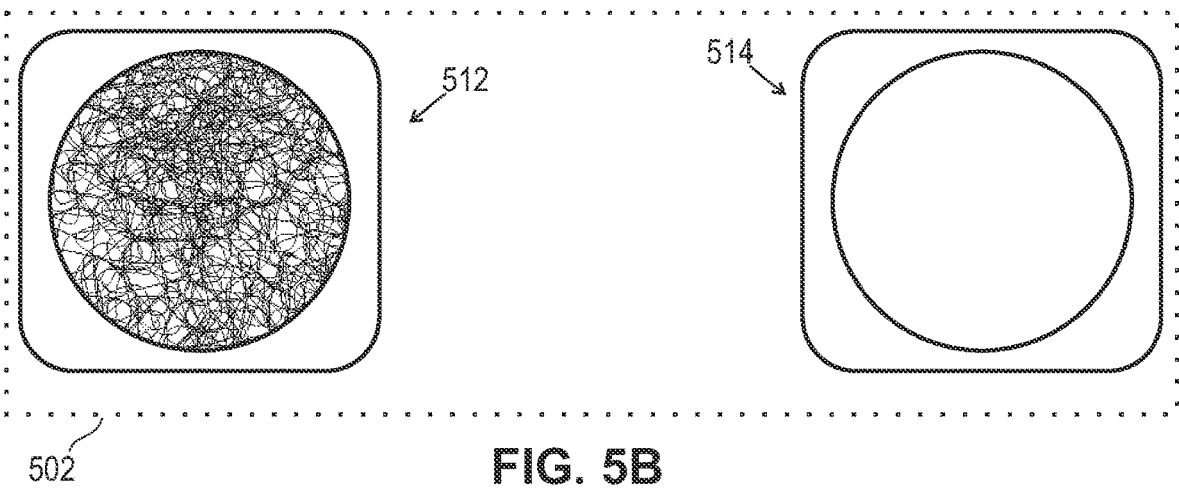
FIGS. 5A and 5B illustrate aerial view representations of a patient utilizing a HMD to undergo a RAPD eye test in accordance with aspects of the disclosure.
Figure 5A:
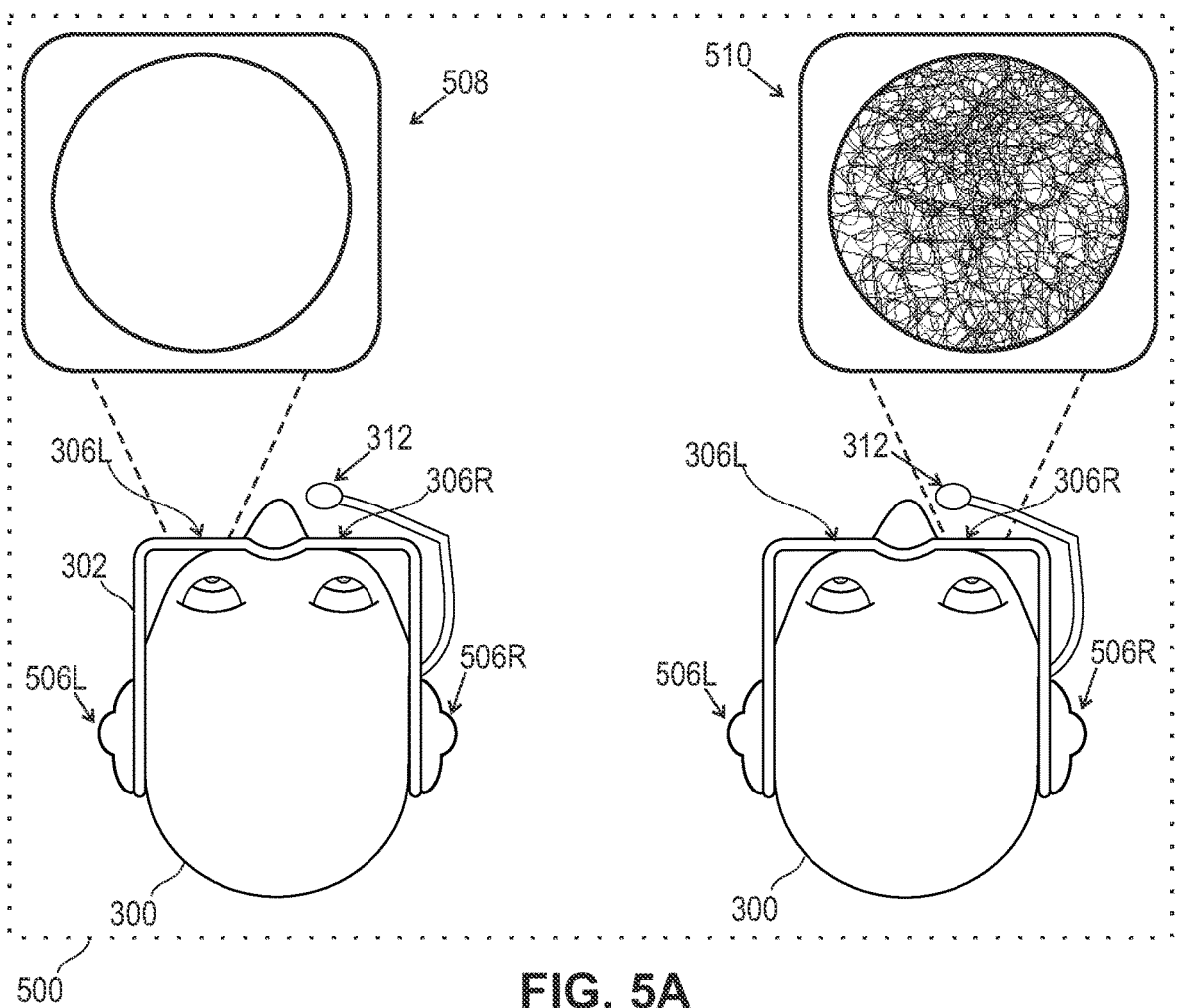

FIGS. 5A and 5B are aerial view representations 500, 502 of a patient 300 utilizing a HMD to undergo a RAPD eye test in accordance with the disclosure. Specifically, FIGS. 5A and 5B illustrate how the RAPD test is administered for determining the relative pupillary responses to the visual stimulus. In general, as explained above the RAPD test measures the relative difference in constriction of the patient's pupil when the light to each eye changes. In the example shown in FIGS. 5A and 5B, the patient 300 wears the HMD 302 and finds himself or herself inside a virtual room, and the HMD 102 is configured to project an image of a bright light to each eye separately in rapid succession.

Referring again to FIG. 5A, in accordance with methods described herein the patient 300 wears the HMD 302 so that optical displays 306R and 306L are positioned in front of his or her right eye and left eye, respectively. In addition, the patient may adjust the headphones or speakers 506L and 506R to position them comfortably over his or her left and right ears, respectively. The patient may also be prompted, via a voice prompt through the speakers 506L and 506R, to adjust the interior cameras (not shown) so that they are positioned directly in front of his or her eyes to improve the accuracy of the measurements taken of the pupil diameters of both eyes during the RAPD test. In other implementations, an eye care professional may assist the patient in donning the HMD 302 so that accurate measurements can be obtained during eye testing.

In some embodiments, a RAPD test may begin with the patient first listening to prerecorded audio instructions explaining the eye testing process and/or procedures that will be used during the eye examination. In some implementations, a RAPD module for conducting this eye test may be downloaded from an application store (an "App store" such as iTunes™ or Google Play™) to the HMD 302 and then utilized to test the patient's eyes. In some embodiments, an eye-tracking feature of the HMD 302 and/or of the visual acuity module is used to ensure compliance by the patient with the testing procedures. Specifically, as instructions are provided to the patient concerning reading a particular pattern or patterns on the RAPD test screen, which is displayed on an interior optical display surface (306R, 306L or both) of the HMD 302, one or more integrated interior cameras (not shown) of the HMD 302 tracks infrared (IR) reflections from the patient's eye and processes that data to determine where the patient's eye is looking at any point in time during the eye test. Then, as shown in FIG. 5A a bright light 508 is projected into the left eye of the patient while darkness 510 is presented to the right eye of the patient. Next, as shown in FIG. 5B the left eye of the patient is presented with a bright light 514 while the right eye is presented with darkness 512. Pupillary response data from the RAPD test may then be used, for example, by an eye doctor to assess one or more of optic nerve function by determining a relative pupillary light response difference between optic nerve of the first eye and optic nerve of the second eye, early glaucoma by determining a relative pupillary light response difference between eye functions of the first eye and eye functions of the second eye, retinal function by determining a relative pupillary light response difference between retina of the first eye and retina of the second eye, foveal function by determining a relative pupillary light response difference between fovea of the first eye and fovea of the second eye, and color sensitivity by determining a relative pupillary light response difference between color responses in the first and second eyes.

In other aspects, the HMD 302 may be used to present successive light/darkness or different patterns of light/darkness to the right eye and to the left eye of a patient in an alternating manner. For example, the light presented to the patient's eyes in an alternating manner may be a full bright light or may be a pattern such as a checkerboard pattern. In some implementations, flashing lights may be presented to the patient.

Some alternatives to traditional eye examinations typically fail to adequately control or account for conditions that impact test results, such as room ambient lighting conditions, room glare, image brightness, humidity, and the like. For example, some Smartphone applications are unable to account for glare on the Smartphone screen or to determine whether or not the patient has completely covered one eye during testing of the other eye. However, testing utilizing an HMD 302 as described herein allows for conditions and contaminants to be closely monitored and/or to be kept consistent and/or to be standardized which is important, for example, for accurately comparing the eye test results to prior eye test results of the patient for determining whether or not there are any discrepancies and/or changes in the patient's eye responses. For example, the HMD 302 depicted in FIG. 5A is configured to prevent glare while conducting an eye examination. Thus, the RAPD eye test results may be relied upon as being standardized and accurate.

In addition, if a patient uses corrective lenses, then that patient may choose to wear their eye glasses underneath the HMD 302 during testing. Alternately, in some implementations that patient's lens specification can be utilized by the HMD to augment the virtual environment and virtual displays in the same manner that their corrective lenses would serve.

With regard to the RAPD test, in some embodiments if the results of the RAPD test indicates that there may be a problem with the patient's eyes, then another RAPD test may be run on the patient in rapid succession. Then, if there is a significant difference between the performance of the consecutive tests, the HMD 302 may transmit a warning message to the physician's or clinician's electronic device that includes these results. In addition, in some implementations the dilation rate differences and responses of the patient to the RAPD test(s) may be stored in a database or other storage device for future comparison and/or analysis.

In accordance with a thorough neurological examination, a Pattern RAPD test may be administered by presenting patterns of light to a patient. The Pattern RAPD module may be downloaded to the HMD 302 which then, in some embodiments, displays a pattern of light in a virtual environment during testing of each eye of the patient. The patterns of light presented to the patient tests the patient's visual fields and the HMD 302 detects responses to a particular region of the pathway in the neuro-ocular anatomy. For example, a semi-circular light pattern (covering the left/right hemi-field, or half of the field of vision) may be shown to the patient to determine if the left/right hemi-field on the retina is responsive to light. The patient's response is recorded, and if his or her performance in one eye is significantly different than the other eye then the eye doctor or physician is notified.

An example of another eye test module that can be downloaded to the HMD 302 is a color vision response module. The color vision response test, known as the Ishihara color patterns test, measures a patient's ability to tell the difference among colors based on pupillary responses. In some implementations, each of the patient's eyes is tested separately using the HMD 302. A series of virtual test cards are presented to the patient, wherein each test card contains a multicolored dot pattern that contains a number or a symbol within the color pattern. The virtual test cards containing the multicolored dot pattern with an embedded symbol are serially displayed to each eye separately and the pupillary responses are collected. If a particular patient cannot see the numbers and/or symbols embedded within the multicolored dot pattern, then pupillary responses from the left and/or the right eye of that patient will deviate from a normal response indicating a color vision impairment. The color vision test may also reveal that the patient has normal color vision but still experiences a loss of color intensity in one eye or the other eye. If the patient does not pass this test, he or she may have poor color vision or may be color blind.

Figure 6:
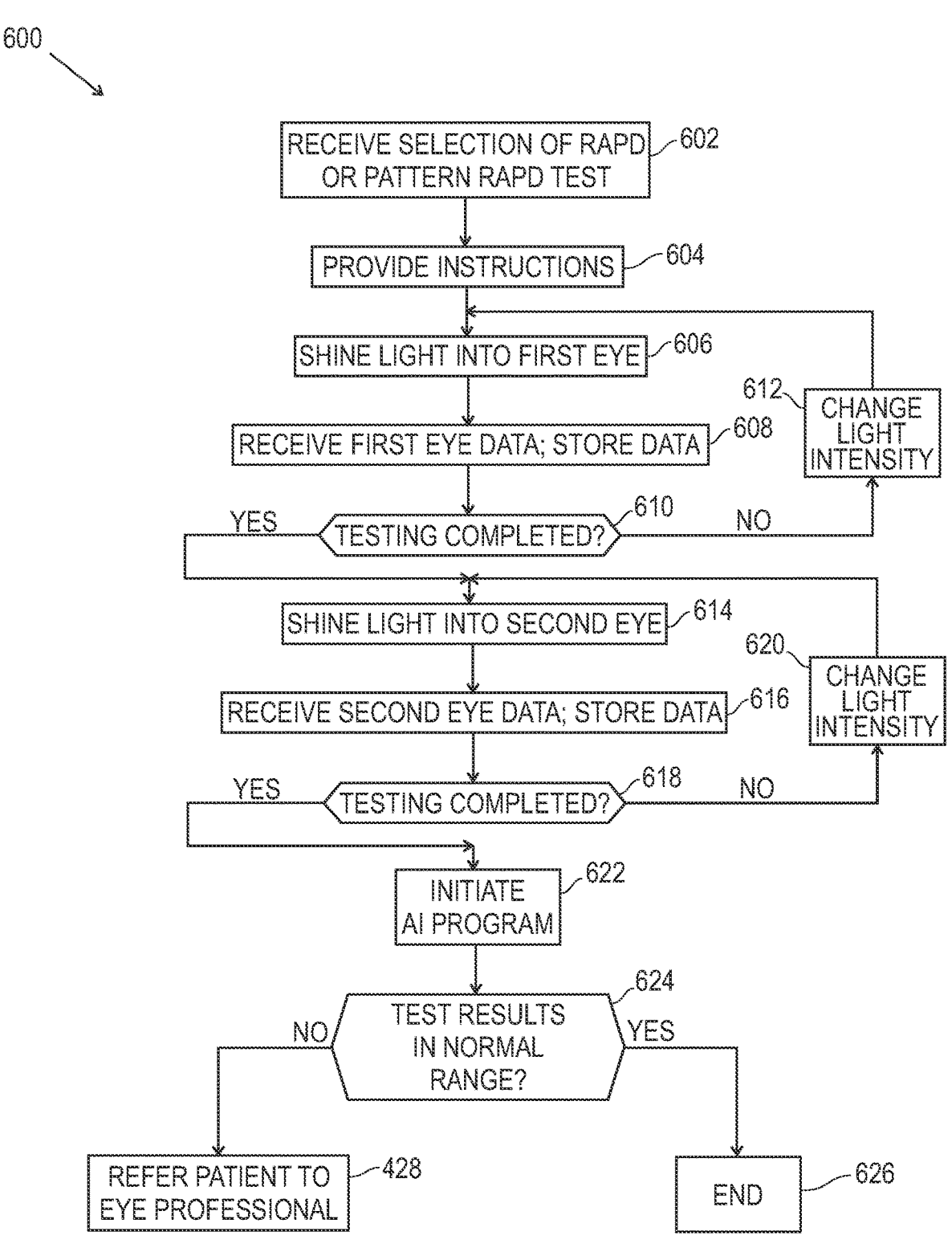
FIG. 6 is a flowchart of a process for generating eye testing procedures and producing pupillary properties, data and parameters for a patient based on one or more RAPD examinations in accordance with aspects of the disclosure.

FIG. 6 is a flowchart 600 of a process for generating eye testing procedures and producing pupillary properties, data and parameters for a patient based on one or more RAPD examinations in accordance with the disclosure. In an implementation, a patient wears a HMD which receives 602 a selection of a RAPD or Pattern RAPD eye test by the patient, or by an eye doctor or clinician, or automatically. Eye test instructions or information may then be audibly provided 604 to the patient via speakers, or may be visually presented to the patient by the HMD. Next, the HMD shines 606 a light into a first eye of the patient, and an interior camera of the HMD receives or collects 608 first eye data from the patient undergoing the RAPD test. In embodiments, the HMD saves or stores the RAPD test data concerning the diameter and/or the rate of constriction of the pupil in a storage device or memory. In addition, in some implementations the HMD transforms the received RAPD test data and stores it as pupillometry parameters which are based on patient vision parameters. In some cases, the transformation includes generating pupillometry parameters that redistribute the color palate of the scene to accommodate for a patient who suffers from color sensitivity losses, for example, color blindness or cataracts. The RAPD test may include the color palate by an eye doctor or other eye professional when it is indicated for the patient.

Referring again to FIG. 6, in some implementations in step 610, if testing of the first eye is not completed then the HMD changes 612 the light intensity and the process branches back to step 606 wherein light of the changed intensity is shined into the first eye of the patient.

In some implementations this light intensity changes occur in rapid succession, while in others the succession will be slower to assess different anomalies. In some implementations the light intensity will be increased to determine the rate of pupil constriction. In other implementation the light intensity decreases in order to evaluate the rate of pupil dilation. Next, RAPD eye test data are again received 608 and stored for the new light intensity.

After testing is completed 610 for the first eye, the RAPD eye test process includes the HMD shining light 614 into the second eye of the patient of the same light intensity and/or pattern presented to the first eye. The process continues with receiving 616 the visual input data from the second eye of the patient by the interior camera of the HMD, and storing the RAPD test data concerning the diameter and/or the rate of constriction of the pupil in a storage device or memory as described earlier for the first eye. Thus, pupillary parameters and data (concerning the diameter and/or the rate of constriction of the pupil) for the second eye are collected and stored. If testing of the second eye is not completed 618, then the intensity of the light is changed 620 by the HMD in accordance with the same testing procedures applied to the first eye and the process branches back to step 614 wherein the HMD shines light of the changed intensity into the second eye of the patient and RAPD eye test data are again collected 616 and stored. The number of times that the light intensity is changed and data is collected is the same as that accomplished for the first eye of the patient in accordance with RAPD eye test procedures.

Referring again to step 618, when testing of both the first eye and the second eye of the patient is completed, then an Artificial Intelligence (AI) program is initiated 622 which accesses the stored pupillary data for both the first and second eyes (the right and left eyes of the patient) and processes that data. Specifically, if the AI program determines 624 that the test results are within a normal range then the RAPD eye test ends 626. In some implementations, this means that the AI program determines that the relative differences in pupillary reflexes are within a predetermined range indicating that the patient's eyes are healthy. The "normal range" is dependent on each individual patient and can be established by first calibrating that individual's ocular anatomy. The calibration can occur by providing each eye with the same light and then measuring pupil parameters.

Referring again to FIG. 6, if the AI program determines 624 that the relative differences in pupillary reflexes of the eyes of the patient are not within a normal range, then the patient may have a neurological deficit and/or disorder involving one or both eyes, and thus the patient is referred 628 to an eye professional, such as an eye doctor or clinician for further assessments. For example, an indication that the patient may have an issue would be if the AI program determine that there is a deviation between the relative pupillary reflexes of the first eye and the second eye of the patient in response to the light stimulus described above. In some embodiments, the AI program may be part of the RAPD test module being run by the HMD, or may be run by another electronic device, such as a server computer, that has access to the stored pupillary data 610 of the patient being tested.

Figure 7:
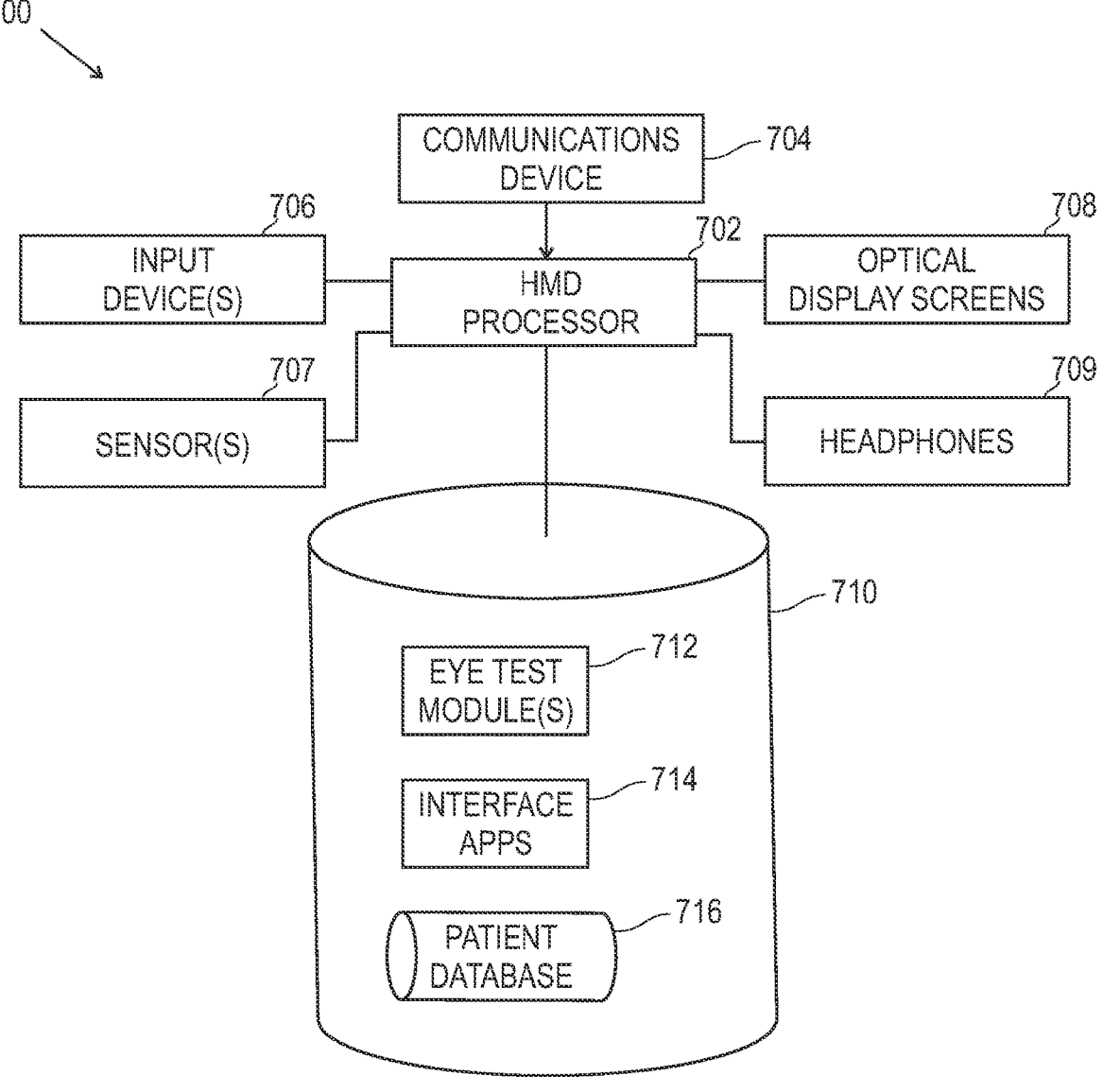
FIG. 7 is a block diagram illustrating the components of a HMD of a type configured to operate in a manner consistent with aspects of the disclosure.

FIG. 7 is a block diagram 700 of an example embodiment of the components of a HMD of a type configured to operate in a manner consistent with processes described herein. The HMD 700 includes a HMD processor 702 operatively coupled to a communication device 704, one or more input devices 706 (such as a camera and/or a microphone), one or more sensors 707, optical display screens (one for each eye of a patient) 708, headphones 709 (or speakers, for example, a speaker for each ear of the patient), and a storage device 710. The HMD processor 702 may constitute one or more processors, which may be custom designed and/or optimized to execute HMD instructions and/or processor-executable instructions and/or steps, which may be contained in program instructions so as to control the HMD 700 provide desired functionality.

Communication device 704 may be used to facilitate communication with, for example, other electronic or digital devices such as other components of the system 400 shown in FIG. 4. Thus, communication device 704 may comprise various and/or numerous communication ports (not separately shown), to allow the HMD 700 to communicate simultaneously with a considerable number of other computers or electronic devices, and/or to simultaneously handle numerous functions including eye testing functions. The communication device 704 may also be configured for wireless communications and/or wired communications via various different types of networks, such as the Internet.

The input devices 706 may include one or more of any type of peripheral device typically used to input data into an HMD or into a computer. For example, the input device 706 may include a camera, a microphone and/or hand controller(s), and/or a touchscreen. The one or more sensors 707 may include, for example, a camera to record patient interactions during eye testing and/or a temperature sensor to record the testing environment temperature.

Storage device 710 may be any appropriate information storage device, including combinations of magnetic storage devices (e.g., hard disk drives), optical storage devices such as CDs and/or DVDs, and/or semiconductor memory devices such as Random Access Memory (RAM) devices and Read Only Memory (ROM) devices, solid state drives (SSDs), as well as flash memory or other type of memory or storage device. Any one or more of such information storage devices may be considered to be a non-transitory computer-readable storage medium or computer usable medium or memory.

Storage device 710 stores one or more programs, program modules and/or applications (Apps) for controlling the HMD processor 702. The programs, program modules and/or Apps comprise program instructions (which may be referred to as computer readable program code means) that contain processor-executable process steps of the HMD 700 which are executed by the HMD processor 702 to cause the HMD 700 to function as described herein.

The programs may include one or more conventional operating systems (not shown) that control the HMD processor 702 so as to manage and coordinate activities and sharing of resources in the HMD 700, and to serve as a host for application programs (described below) that run on the HMD 700.

The storage device 710 may also store one or more eye test modules 712 which include processor-executable instructions for administering one or more eye tests as described herein to a patient, recording the outcome(s), and in some cases contacting an eye doctor, clinician or other medical professional. In addition, the storage device 710 may also store interface applications 714 which include executable instructions for providing software interfaces to facilitate interaction(s) between a patient being tested by use of one or more eye test modules and other components of the system 400.

The storage device 710 may also store, and HMD 700 may also execute, other programs, which are not shown. For example, such other programs may include HMD display device drivers, database management software, and the like.

Moreover, the storage device 710 may also store a patient data database 716 for storing patient eye test data, such as results of specific eye tests such as the RAPD eye tests described herein, whether or not an eye doctor was notified of the eye test results, and the like. In addition, one or more further databases (not shown) needed for operation of the HMD 700 may also be included.

Accordingly, the systems and processes disclosed herein solve the technological problem of how to quickly and accurately test relative afferent pupillary defects (RAPD) of patients by using the RAPD test and resulting test data to assess and/or diagnose the level of neurological deficits and/or disorders, while at the same time providing flexibility in the administration of eye tests for patients. These goals are achieved by leveraging the visualization, processing, and eye tracking capabilities of a head mounted display (HMD) such as a virtual reality headset to administer, monitor and/or report eye examination data 1. Moreover, eye test modules, which include eye tests administered via an HMD as described herein, advantageously conform to well-established RAPD measurement protocols that include light intensity, illumination, patterns, and color. In addition, in disclosed implementations the eye test methods disclosed herein may include receiving patient input video of each eye, receiving patient audio responses and/or motion controller response. Moreover, in some embodiments the input may be compared to input provided by a machine learning protocol. Eye test results data may also be compared with previous testing results of the patient or of other patients, and/or may be compared to a baseline or to an adjusted baseline, and any significant change in performance or deviation from a normal range may be noted and/or stored. In addition, in some embodiments a test module or artificial intelligence (AI) process is beneficially available and utilized to determine the stage of deterioration of a patient's neurological condition.

As used herein, the term "computer" should be understood to encompass a single computer or two or more computers in communication with each other.

As used herein, the term "processor" should be understood to encompass a single processor or two or more processors in communication with each other.

As used herein, the term "memory" should be understood to encompass a single memory or storage device or two or more memories or storage devices.

As used herein, a "server" includes a computer device or system that responds to numerous requests for service from other devices.

The above descriptions and illustrations of processes herein should not be considered to imply a fixed order for performing the process steps. Rather, the process steps may be performed in any order that is practicable, including simultaneous performance of at least some steps and/or omission of steps.

Although the present disclosure has been described in connection with specific example embodiments, it should be understood that various changes, substitutions, and alterations apparent to those skilled in the art can be made to the disclosed embodiments without departing from the spirit and scope of the disclosure.

What is claimed is:

1. A method for evaluating pupillary responses of a patient comprising:

exposing, by a head mounted display (HMD) worn by a patient that comprises at least one processor, a first optical display, a second optical display, an internal camera, and a communications device, a first eye to light stimulation in accordance with a relative afferent pupillary defects (RAPD) eye test by:

presenting, by the at least one processor, a video recording of an external light source via the first optical display to the first eye of the patient while the second optical display proximate a second eye of the patient is off; and recording, by the internal camera, first pupil light response data from both the first eye and the second eye of the patient;

exposing, by the HMD, the second eye of the patient to the same RAPD eye test by:

turning off, by the at least on processor, the video recording being shown to the first eye of the patient while also presenting the video recording of the external light source via the second optical display to the second eye of the patient; and recording, by the internal camera, second pupil light response data from both the first eye and the second eye of the patient;

generating, by the at least one processor utilizing the first pupil light response data and the second pupil light response data, at least one RAPD test result, wherein the generating the at least one RAPD test result comprises:

determining, by the at least one processor, a center point of the first eye and its pupil within image data of the first eye;

determining, by the at least one processor, a center point of the second eye and its pupil within image data of the second eye;

obtaining, by the first optical display, first image data of a first half of the first eye having an edge defined by a first line of pixels intersecting the determined center point of the first eye;

obtaining, by the second optical display, second image data of a second half of the second eye, the second half of the second eye opposing the first half of the first eye and having an edge defined by a second line of pixels intersecting the determined center point of the second eye; and generating, by the at least one processor using the first image data and the second image data, a composite image of the patient's eyes and pupils.

2. The method of claim 1, further comprising transmitting, by the at least one processor, the at least one RAPD test result to a second computer for evaluation.

3. The method of claim 1, wherein the at least one RAPD test result comprises pupillary light response data used to assess at least one of:

optic nerve function by determining a relative pupillary light response difference between optic nerve of the first eye and optic nerve of the second eye;

early glaucoma by determining a relative pupillary light response difference between eye functions of the first eye and eye functions of the second eye;

15

16 retinal function by determining a relative pupillary light response difference between retina of the first eye and retina of the second eye;

foveal function by determining a relative pupillary light response difference between fovea of the first eye and fovea of the second eye; and color sensitivity by determining a relative pupillary light response difference between color responses in the first and second eyes.

4. The method of claim 1, wherein the at least one RAPD test result comprises pupillary light response data used to assess at least one of:

a brain tumor by determining a relative pupillary light response difference between the first eye and the second eye of the patient to determine which half of the brain receiving signals from the eyes may have tumors; and an aneurysm by determining a relative pupillary light response difference between the first eye and the second eye of the patient to determine which half of the brain receiving signals from the eyes may have an aneurysm.

5. The method of claim 1, wherein the at least one RAPD test result comprises pupillary light response data used to assess processes affecting at least one of optic nerve, optic chiasm, or optic radiations by determining a relative pupillary light response difference between the first eye and the second eye of the patient responsible for transmitting light signals via at least one of the optic nerve, the optic chiasm, or other optic pathways to the brain.

6. A head-mounted display (HMD) device for evaluating pupillary responses of eyes of a patient comprising:

a frame configured to be worn by a patient;

a first eye scope including a first ocular aperture, a first light aperture and a first monitoring aperture, the first eye scope operably connected to the frame;

a second eye scope including a second ocular aperture, a second light aperture and a second monitoring aperture, the second eye scope operably connected to the frame;

an HMD processor operably connected to the first eye scope and the second eye scope; an internal camera operably connected to the HMD processor; and a storage device operably connected to the HMD processor and storing processor executable instructions which when executed causes the HMD processor to:

expose a first eye of the patient to light stimulation in accordance with a relative afferent pupillary defects (RAPD) eye test by:

presenting, by the HMD processor, a video recording of an external light source via the first eye scope to the first eye of the patient while the second eye scope proximate a second eye of the patient is off; and recording, by the internal camera, first pupil light response data from both the first eye and the second eye of the patient;

expose a second eye of the patient to light stimulation in accordance with the same RAPD eye test by:

turning off, by the HMD processor, the video recording being shown to the first eye of the patient while also presenting the video recording of the external light source via the second eye scope to the second eye of the patient; and recording, by the internal camera, second pupil light response data from both the first eye and the second eye of the patient; and generate, by the HMD processor utilizing the first pupil light response data and the second pupil light response data, at least one RAPD test result, wherein the generating the at least one RAPD test result comprises:

determining, by the at least one processor, a center point of the first eye and its pupil within image data of the first eye;

determining, by the at least one processor, a center point of the second eye and its pupil within image data of the second eye;

obtaining, by the first optical display, first image data of a first half of the first eye having an edge defined by a first line of pixels intersecting the determined center point of the first eye;

obtaining, by the second optical display, second image data of a second half of the second eye, the second half of the second eye opposing the first half of the first eye and having an edge defined by a second line of pixels intersecting the determined center point of the second eye; and generating, by the at least one processor using the first image data and the second image data, a composite image of the patient's eyes and pupils.

7. The device of claim 6, further comprising a communications device operably connected to the HMD processor, and wherein the storage device stores further processor executable instructions which when executed causes the HMD processor to transmit the RAPD test result to a second computer for evaluation via the communication device.

8. The device of claim 6, further comprising a light source connected to the frame and operably connected to the HMD processor, wherein the light source is utilized instead of the video recording of the external light source to expose the first eye of the patient and the second eye of the patient to light stimulation under control of the HMD processor.

9. The device of claim 6, further comprising headphones operably connected to the HMD processor, and wherein the storage device stores further processor executable instructions which when executed causes the HMD processor to provide RAPD eye test audio instructions to the headphones.

10. The device of claim 6, further comprising at least one sensor operably connected to the HMD processor.

11. The device of claim 10, wherein the at least one sensor comprises at least one of a temperature sensor, a humidity sensor, a light sensor, and a camera.

12. The device of claim 11, wherein the at least one sensor comprises a temperature sensor and wherein the storage device stores further processor executable instructions which when executed causes the HMD processor to obtain and transmit ambient temperature data associated with a testing environment to a second computer.

13. The device of claim 11, wherein the at least one sensor comprises a humidity sensor and wherein the storage device stores further processor executable instructions which when executed causes the HMD processor to obtain and transmit humidity data associated with a testing environment to a second computer.

14. The device of claim 11, wherein the at least one sensor comprises a light sensor and wherein the storage device stores further processor executable instructions which when executed causes the HMD processor to obtain and transmit light sensor data concerning an ambient light level of a testing environment to a second computer.

15. The device of claim 11, wherein the at least one sensor comprises a camera and wherein the storage device stores further processor executable instructions which when executed causes the HMD processor to obtain and transmit a picture of a testing environment to a second computer.

16. The device of claim 6, wherein the at least one RAPD test result comprises pupillary light response data used to assess at least one of:

optic nerve function by determining a relative pupillary light response difference between optic nerve of the first eye and optic nerve of the second eye;

early glaucoma by determining a relative pupillary light response difference between eye functions of the first eye and eye functions of the second eye;

retinal function by determining a relative pupillary light response difference between retina of the first eye and retina of the second eye;

foveal function by determining a relative pupillary light response difference between fovea of the first eye and fovea of the second eye; and color sensitivity by determining a relative pupillary light response difference between color responses in the first and second eyes.

17. The device of claim 6, wherein the at least one RAPD test result comprises pupillary light response data used to assess at least one of:

a brain tumor by determining a relative pupillary light response difference between the first eye and the second eye of the patient to determine which half of the brain receiving signals from the eyes may have tumors; and an aneurysm by determining a relative pupillary light response difference between the first eye and the second eye of the patient to determine which half of the brain receiving signals from the eyes may have an aneurysm.

* * * * *